United States Patent [19]

Fischer et al.

[11] 4,450,108

[45] May 22, 1984

[54] PYRROLOBENZOTRIAZEPINES

[75] Inventors: Rudolf Fischer, Kehrsatz; Franz M. Künzle, Berne; Jean Schmutz, Muri, all of Switzerland

[73] Assignee: Sandoz Ltd., Basel, Switzerland

[21] Appl. No.: 217,528

[22] Filed: Dec. 17, 1980

[30] Foreign Application Priority Data

Dec. 21, 1979 [CH] Switzerland ................. 11415/79

[51] Int. Cl.³ .................................. C07D 403/14
[52] U.S. Cl. ............................ 260/243.3; 424/249
[58] Field of Search ........................... 260/243.3

[56] References Cited

U.S. PATENT DOCUMENTS 3,984,562 10/1976 Wright .................... 260/243.3
4,097,597 6/1970 Hurrom et al. .......... 260/243.3

Primary Examiner—Donald G. Daus
Assistant Examiner—D. B. Springer
Attorney, Agent, or Firm—Gerald D. Sharkin; Robert S. Honor; Joseph J. Borovian

[57] ABSTRACT

A pyrrolobenzotriazepine or a pharmaceutically acceptable acid addition salt thereof is useful as a neuroleptic, anti-depressant or soporific.

12 Claims, No Drawings

PYRROLOBENZOTRIAZEPINES

The present invention relates to pyrrolobenzotriazepines, their production and pharmaceutical compositions containing them.

The present invention provides 11-piperazinyl-5H-pyrrolo[1,2-b][1,2,5]benzotriazepines, hereinafter referred to as compounds of the invention. It is to be appreciated that a compound of the invention may be optionally substituted in any available position.

The present invention in particular provides compounds of formula I,

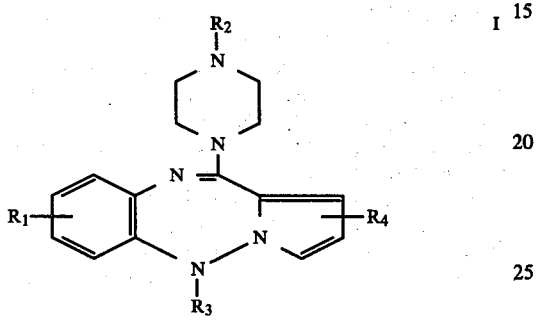

wherein
- $R_1$ and $R_4$ are each independently hydrogen, halogen, $(C_{1-4})$alkyl, $(C_{1-4})$alkoxy, $(C_{1-4})$alkylthio or trifluoromethyl,
- $R_2$ is hydrogen, $(C_{1-4})$alkyl, $(C_{2-4})$hydroxyalkyl or a physiologically acceptable hydrolyzable ester thereof, and
- $R_3$ is hydrogen, $(C_{1-4})$alkyl, $(C_{3-5})$alkenyl or benzyl.

In formula I any alkyl, alkoxy or alkylthio radical of 1 to 4 carbon atoms has preferably 1 to 3 carbon atoms, especially 1 and 2 carbon atoms. Hydroxyalkyl has preferably 2 or 3 carbon atoms and preferably the hydroxy group in free form or in esterified form is attached to a carbon atom other than the carbon atom adjacent to the nitrogen atom. Halogen means fluorine, chlorine, bromine or iodine. Halogen is conveniently fluorine, chlorine or bromine, preferably fluorine or chlorine, and especially chlorine. The double bond of alkenyl is preferably not in the $\alpha,\beta$-position. Alkenyl is conveniently allyl or 2-methylallyl.

Physiologically hydrolyzable esters are those esters which under physiological conditions are split to the corresponding compounds having a hydroxyalkyl piperazinyl group. Such esters are particularly derived from $(C_{2-18})$alkanoic, $(C_{3-7})$-cycloalkylcarboxylic, benzoic, phenyl$(C_{2-7})$alkanoic, benzoic or phenyl$(C_{2-7})$alkanoic acids, optionally monosubstituted in the phenyl ring by $(C_{1-4})$-alkyl or mono- or independently disubstituted in the phenyl ring by halogen, or mono- or independently di- or independently trisubstituted in the phenyl ring by $(C_{1-4})$alkoxy.

$R_1$ is conveniently in position 8. $R_1$ is conveniently halogen. $R_2$ is conveniently alkyl. $R_3$ is conveniently alkyl. $R_4$ is conveniently hydrogen. When it is other than hydrogen, it is conveniently in position 2 or 3.

The present invention in another aspect provides a process for the production of a compound of the present invention which comprises
(a) reacting an appropriate 5H-pyrrolo[1,2-b][1,2,5]benzotriazepine derivative having a leaving group or a carbonyl group in the 11 position with an appropriate piperazine, or
(b) cyclising a 1-[2-(N-1-pyrrolyl)amino]-phenylaminocarbonyl piperazine derivative.

In particular a compound of formula I as defined above may be produced by a process which comprises
(a) obtaining a compound of formula Ia,

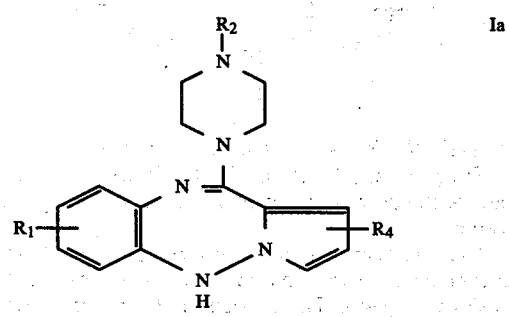

wherein $R_1$, $R_2$ and $R_4$ are as defined above, by reacting a compound of formula II,

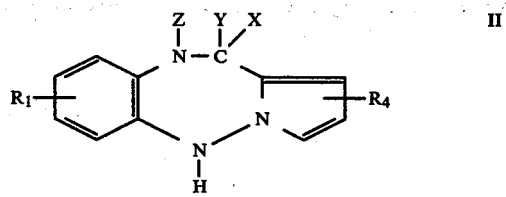

wherein $R_1$ and $R_4$ are as defined above, and either
(i) Z and Y together form a single bond and X is a leaving group, or
(ii) Z is hydrogen and Y and X together with the carbon atom to which they are bound are $>C=O$,
with a compound of formula III,

wherein $R_2$ is as defined above, or
(b) obtaining a compound of formula Ib,

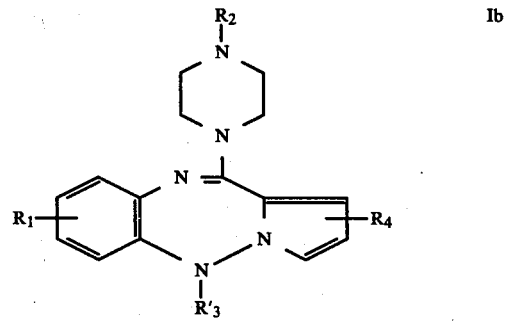

wherein $R_1$, $R_2$ and $R_4$ are as defined above and $R_3'$ has the same significance as $R_3$ except that it is not hydrogen, by cyclising a compound of formula IV,

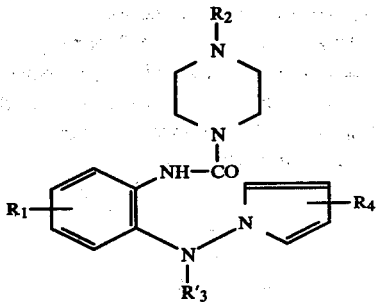

wherein $R_1$, $R_2$, $R_3'$ and $R_4$ are as defined above.

The process (a) may be effected in conventional manner for the production of similar compounds by condensation.

The reaction of a 5H-pyrrolo[1,2-b][1,2,5]benzotriazepine derivative having a leaving group in the 11 position, in particular compound of formula II, wherein Z and Y together form a single bond and X is a leaving group, such as halogen, especially chlorine, sulfhydril, $(C_{1-4})$alkoxy or $(C_{1-4})$alkylthio, p-nitrobenzylthio or tosyloxy, is conveniently carried out in an inert organic solvent such as xylene, toluene or dioxane at a temperature of from 50° to 170° C. When a 5H-pyrrolo[1,2-b][1,2,5]benzotriazepine derivative having a carbonyl group in the 11 position, in particular compound of formula II, wherein Z is hydrogen and Y and X together with the carbon atom to which they are bound are $>C=O$ is used as starting material then the compounds of formula III are conveniently employed as metal complexes comprising a metal of the group IVb of the periodic system, or vanadium. The reaction is conveniently then carried out in the presence of an acid-binding agent, e.g. triethylamine, pyridine, dimethylaniline, or an excess of the compound of formula III. Preferably titanium is used as the metal. Conveniently the complex is obtained from the metal tetrachloride.

Process (b) may be effected in conventional manner. The cyclisation is preferably carried out by heating in the presence of zinc chloride, aluminium chloride, phosphoric acid, polyphosphoric acid and the like, especially phosphorus oxychloride or phosphorus oxychloride and phosphorus pentoxide, if desired in an inert solvent, such as benzene or toluene.

The compounds of formula II with the significance (i) may be prepared from the corresponding compounds of formula II with the significance (ii). The latter may be obtained, for example, as in the following scheme:

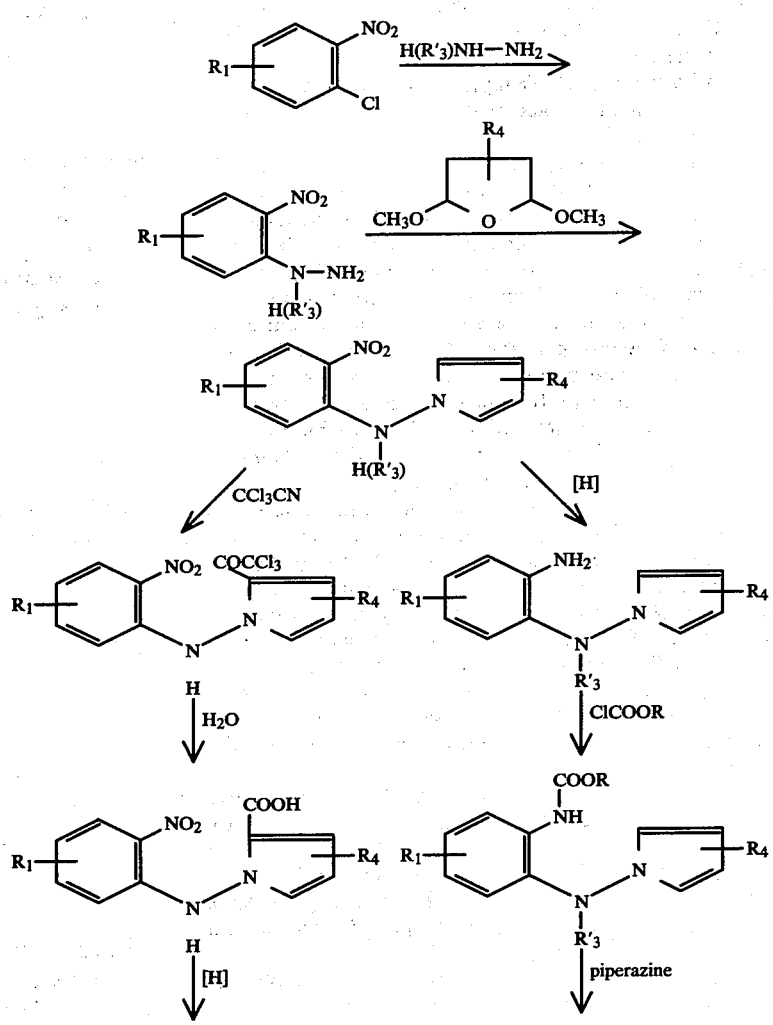

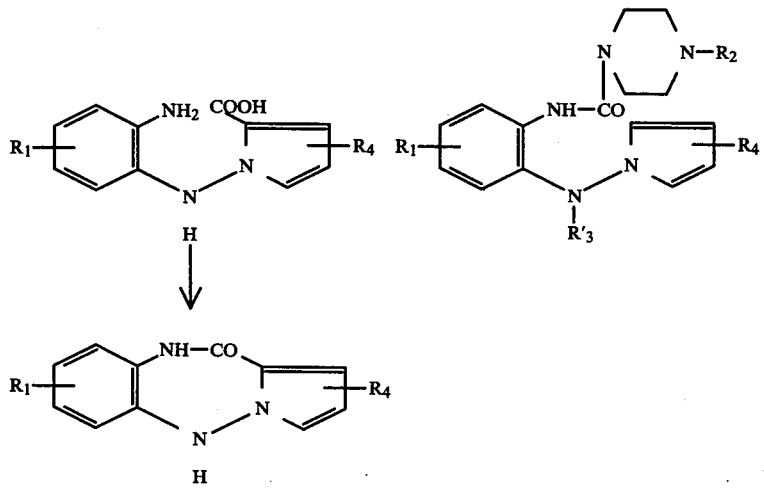

Insofar as the production of starting materials is not particularly described these compounds are known or may be produced in analogous manner to known compounds or to processes described herein.

Free base forms of the compounds of the invention may be converted into acid addition salt forms in conventional manner and vice versa. Suitable acids are e.g. maleic acid, succinic acid, methanesulphonic acid, hydrochloric acid and hydrobromic acid.

In one group of compounds $R_1$ is hydrogen, halogen or trifluoromethyl and each of $R_2$, $R_3$ and $R_4$ is independently, hydrogen or alkyl.

In the following Examples the temperatures given are in degrees Centigrade and are uncorrected.

EXAMPLE 1

8-Chloro-5-methyl-11-(4-methyl-1-piperazinyl)-5H-pyrrolo[1,2-b][1,2,5]benzotriazepine 68.5 g of 1-methyl-4-[(2-(N-methyl-N-1-pyrrolyl)-amino-5-chloro)-anilino]carbonyl-piperazine and 950 ml of phosphorus oxychloride are refluxed 1½ hours. Excess phosphorus oxychloride is removed from the reaction mixture in a slowly increasing vacuum at 80°. The residue is dissolved in 400 ml chloroform and the chloroform solution is added to 2 ltr. of 60° warm water dropwise, at such a rate to maintain a constant and regular distillation of chloroform. The temperature is then raised to 70° and then cooled to 50°. The mixture is treated with 1-2 g of sodium dithionite, charcoal and filtered. The cold filtrate is washed 3 times with each 100 ml ether, then made alkaline with concentrated sodium hydroxide and extracted 3 times with each 500 ml ether. The ether phases are washed with water and brine, dried, treated with charcoal and filtered through aluminium oxide. The filtrate is evaporated to dryness and the residue recrystallised from petroleum ether to give the heading compound, m.p. 113°–115°. M.p. of the succinate 149°–151°.

The starting material 1-methyl-4-[(2-N-methyl-N-1-pyrrolyl)-amino-5-chloro)-anilino]-carbonyl-piperazine may be obtained as follows: (a) N-methyl-N-(2-nitro-4-chlorophenyl)hydrazine 72 g methylhydrazine are added dropwise within 15 minutes to a refluxed mixture of 150 g 2,5-dichloro nitro benzene in 300 ml n-propanol. The mixture is refluxed for 10 hours and left overnight at room temperature. The solution is decanted from the resulting precipitate and evaporated to dryness. The residue is combined with the precipitate, suspended in 400 ml water and extracted twice with each, 1 ltr. ether. The combined ether phases are treated with charcoal, treated with aluminum oxide, concentrated, cooled in ice-water and treated portionwise with petroleum ether. The resulting crystallisate is filtered off and recrystallised from ether/petroleum ether to give the heading compound, m.p. 89°–91°.

(b) 1-[N-methyl-N-(2-nitro-4-chlorophenyl)]-aminopyrrole

A mixture of 102.5 g of the product of step (a), 450 ml glacial acetic acid and 67.4 g 2,5-dimethoxytetrahydrofuran is refluxed for 30 minutes. The solution is evaporated, the residue dissolved in ca. 1 ltr. ether and treated with charcoal. The ether phase is extracted several times with each ca. 50 ml of 2 N sodium hydroxide, then washed with 2 N hydrochloric acid/water and brine, dried and filtered through aluminum oxide. The filtrate is concentrated and cooled with ice/water whereupon the heading compound crystallises out, m.p. 89°–90° (recrystallised from ether/petroleum ether).

(c) 1-[N-Methyl-N-(2-amino-4-chlorophenyl)-]aminopyrrole

A suspension of 99.9 g of the product of step (b) in 750 ml ethyl acetate and several spoonful of Raney nickel is hydrogenated at 30 mm overpression and room temperature until completion of the reaction. The catalyst is filtered off and the filtrate is evaporated in vacuo to dryness to give the heading compound as an oil.

(d) 1-[N-Methyl-N-(2-phenoxycarbonylamino-4-chlorophenyl)]amino-pyrrole

A solution of 12.0 g sodium hydroxide in 120 ml of water and 24 g potassium carbonate are added to a solution of 68 g of the product of step (c) in 750 ml ether. The mixture is cooled to 2° in an ice-bath and under stirring dropwise treated with a solution of 48 g of phenyl chloroformate in 50 ml ether. Stirring is continued at a temperature under 5° for several hours and then overnight at room temperature. The aqueous phase is extracted twice with each 100 ml ether. The ether phase is washed and diluted sodium hydroxide solution, water, dilute hydrochloric acid and brine, dried, treated with charcoal and filtered through aluminum oxide. The filtrate is concentrated and treated with petroleum ether to precipitate the heading compound, m.p. 90°–92°.

(e) 1-Methyl-4-[(2-(N-methyl-N-1-pyrrolyl)-amino-5-choro)-anilino]-carbonyl-piperazine 107.5 g of the product of step (d), 33 g N-methylpiperazine and 1.5 ltr. toluene are heated 10 hours at internal temperature of 80°. To the cold mixture 750 ml of water are added and the water phase is extracted twice with, each 150 ml ether. The ether phases are extracted with 2 N hydrochloric acid, the acid phase is made alkaline with concentrated sodium hydroxide and extracted with ether. The combined ether phases are washed with brine, dried, treated with charcoal and filtered through aluminum oxide. The filtrate is concentrated in vacuo and treated with petroleum ether to give the heating compound, m.p. 79°–80° (recrystallised from ether/petroleum ether).

EXAMPLE 2

11-(4-Methyl-1-piperazinyl)-5H-pyrrolo[1,2-b][1,2,5]benzotriazepine

A solution of 1.4 ml titanium tetrachloride in 12 ml of absolute benzene is added dropwise under stirring at 5° to a mixture of 1.8 g of 5H-pyrrolo[1,2-b][1,2,5]benzotriazepin-11(10H)-one, 5 ml N-methyl-piperazine, 75 ml tetrahydrofuran and 12 ml absolute benzene. The mixture is stirred at 0° for 15 minutes and then refluxed for 4 hours. After the mixture has been cooled, 25 ml of water are added dropwise and the precipitate is filtered off. The 2-phase filtrate is then evaporated and the residue made alkaline with concentrated sodium hydroxide solution and extracted with ether. The ether phase is extracted with 2 N hydrochloric acid, the combined acid phases are made alkaline with concentrated sodium hydroxide solution and extracted with ether. The organic phase is evaporated to dryness to give the heading compound, m.p. 209°–211° (recrystallised from acetone/ether).

The starting material 5H-pyrrolo[1,2-b][1,2,5]benzotriazepine-11(10H)-one may be obtained as follows:

(a) 1-(2-Nitrophenylamino)-2-trichloracetyl pyrrole

A cooled solution of 40.5 g 1-(2-nitrophenylamino)-pyrrole (prepared as described in Example 1b) and 43 g trichloroacetonitrile in 650 ml of absolute ether is saturated with gaseous hydrogen chloride. The mixture is stirred with cooling for 24 hours. Water is added carefully and then ether. The ether phase is washed with brine, dried and concentrated to give the heading compound, m.p. 145°–148° (recrystallised from ether/petroleum ether).

(b) 1-(2-Nitro-phenylamino)-pyrrolo-2-carboxylic acid

To a stirred suspension of 20 g of the product of step (a) in 100 ml water and 45 ml acetone is added dropwise at 40° a solution of 3.5 g sodium hydroxide in 30 ml water. The mixture is heated at 60° for 10 minutes and evaporated. The residue is acidified with conc. hydrochloric acid to give the title compound, m.p. 215°–220° (decomp.).

(c) 1-(2-Amino-phenylamino)-pyrrolo-2-carboxylic acid

A solution of 9 g of the product of step (b) in 300 ml ethanol and 2 g of 5% of palladium-on-carbon is hydrogenated at room temperature and normal pressure. The catalyst is filtered off, the filtrate evaporated and the residue treated with ether. The ether phase is washed with water, dried and evaporated. On addition of petroleum ether the heading compound, m.p. 140°–143° (decomposition) (recrystallised from ether/petroleum ether) precipitates.

(d) 5H-Pyrrolo[1,2-b][1,2,5]benzotriazepin-11(10H)-one

A solution of 6.8 g N,N-dicyclohexylcarbodiimide in 60 ml ethyl acetate is added at 0° dropwise to a stirred suspension of 4.4 g of the product of step (c) and 2.8 g 1-hydroxybenzotriazole in 200 ml ethyl acetate. The mixture is stirred for 2 hours at 0° and 16 hours at room temperature. The precipitated dicyclohexyl urea is filtered off and the filtrate evaporated to give the heading compound, m.p. 225°–230° decomp. (recrystallised from acetone/ether).

EXAMPLE 3

In analogous manner to that described in Example 1, the following compounds of formula I are obtained:

| Ex. | $R_1$ | $R_2$ | $R_3$ | $R_4$ | m.p.* |
|---|---|---|---|---|---|
| a | H | $CH_3$ | $CH_3$ | H | 114–115 |
| b | 8-F | $CH_3$ | $CH_3$ | H | 139–141 |
| c | H | H | $CH_3$ | H | 169–173 |
| d | 8-Cl | $CH_3$ | $CH_3$ | 3-$CH_3$ | 102–105 |
| e | 8-Br | $CH_3$ | $CH_3$ | H | 110–111 |
| f | 8-$CF_3$ | $CH_3$ | $CH_3$ | H | 107–108 |

*free base form

EXAMPLE 4

In analogous manner to that described in Example 2, the following compounds of formula I are obtained:

| Ex. | $R_1$ | $R_2$ | $R_3$ | $R_4$ | m.p. |
|---|---|---|---|---|---|
| a | 8-Cl | $CH_3$ | H | 3-$CH_3$ | |
| b | 8-Cl | $CH_3$ | H | H | |

EXAMPLE 5

In analogous manner to that described in Example 1, the following compounds of formula I may be obtained.

| Ex. | $R_1$ | $R_2$ | $R_3$ | $R_4$ |
|---|---|---|---|---|
| a | 6-OCH($CH_3$)$C_2H_5$ | H | $CH_2C_6H_5$ | 2-S—$iC_3H_7$ |
| b | 7-S—$nC_4H_9$ | H | H | 2-$CF_3$ |
| c | 6-S—n-$C_4H_9$ | H | H | 3-Br |
| d | 9-S—n-$C_4H_9$ | H | H | 3-O—n-$C_4H_9$ |

EXAMPLE 6

The following esters of the compounds of formula I may be obtained:

| Ex. | corresp. compound of formula I (Example No.) | $R_2$ |
|---|---|---|
| a | 2 (c) | $C_3H_6OCO$—n-$C_9H_{19}$ |
| b | 2 (e) | $C_4H_8OCO$—(3-ethylbenzyl) |
| c | 2 (a) | $C_4H_8OCO$—cycloheptyl |
| d | 3 (a) | $C_3H_6OCO$—(2-fluoro-3-chlorophenyl) |
| e | 3 (b) | $C_3H_6OCO$—4-$C_4H_8$—(3,4,5-triethoxyphenyl) |

The compounds of the invention are useful because they possess pharmacological activity in animals and are therefore useful as pharmaceuticals, e.g. for therapy. In particular, the compounds of the invention are useful as neuroleptic agents in the treatment of e.g. psychotic disturbances such as schizophrenia, as indicated in standard tests, e.g. by an inhibition of spontaneous motor activity in mice on p.o. administration of from about 1 to about 50 mg/kg animal body weight of the compounds in accordance with the principles of Caviezel and Baillod (Pharm. Acta Helv. (1958), 33, 465–484). Furthermore, the compounds on administration of 2–20 mg/kg p.o. to rats increase the sleep phase II and decrease the paradoxical sleep in the sleep/wake cycle carried out in accordance with the principles of H. Kleinlogel et al., European J. Pharmacol. 33, 159–163 (1975). Additionally the resulting sleep phase II shows atypical qualitative characteristics.

For the above mentioned use the dosage will, of course, vary depending on the compound employed, mode of administration and therapy desired. However, in general, satisfactory results are obtained with a daily dosage of from about 0.15 mg to about 50 mg per kg animal body weight, conveniently given in divided doses 2 to 4 times a day or in sustained release form. For the larger mammals, the total daily dosage is in the range from about 10 mg to about 1000 mg (e.g. 10 to 500 or 300 to 600 mg), and dosage forms suitable for oral administration comprise from about 2 mg to about 500 mg of the compounds admixed with a solid or liquid pharmaceutical carrier or diluent.

The compounds of the invention are further useful as anti-depressant agents as indicated in standard tests, for example, by an inhibition of cortical noradrenaline uptake both in vitro and as a consequence of in vivo pretreatment. In the first test the compounds (300–50,000 nM) were incubated with rat cortical slices in Krebs-Henseleit solution pH 7.4 and 0.09 nM $^3$H-noradrenaline solution. The cortices were washed with fresh Krebs-Henseleit solution, homogenized and the retained $^3$H-noradrenaline estimated by scintillation counting. In a second test rats were killed 1 hour after the i.p. administration of 40 to 150 mg/kg of the test substance and the in vitro uptake of $^3$H-noradrenaline in the cortical slices determined as previously described.

The compounds inhibit the tetrabenazine-induced catalepsy and ptosis in rats on i.p. administration of from 5 to 15 mg/kg animal body weight of the compound in accordance with the method described by Stille (Arzneimittel-Forsch. 1964, 14, 534).

For the above-mentioned use the dosage will, of course, vary depending on the compound employed, mode of administration and condition to be treated. However, in general satisfactory results are obtained with a daily dosage of from about 0.1 to about 150 mg/kg animal body weight, preferably given in divided doses 2 to 4 times a day, or in sustained release form. For the larger mammals the total daily dosage is in the range from about 10 to about 1,000 mg (e.g. 10 to 500 mg) and dosage forms suitable for oral administration comprise from about 2 to about 250 mg of the compound admixed with a solid or liquid pharmaceutical carrier or diluent.

Additionally the compounds of the invention are useful as sleep-inducing, sleep-promoting and sleep-prolonging agents in the treatment of e.g. insomnia, as indicated in standard tests. For example, in the test mentioned above an increase in the sleep phase II and a decrease of the wake phase is observed after administration to rats of from 2 to 80 mg/kg p.o. animal body weight of the compounds.

For the above-mentioned use the dosage will, of course, vary depending on the compound employed, mode of administration and therapy desired. However, in general, satisfactory results are obtained with a daily dosage of from 0.1 mg to about 80 mg per kg animal body weight, conveniently given shortly before retiring to sleep. For the larger mammals, the total daily dosage is in the range from about 10 to about 100 mg.

The compounds of the invention may be administered in pharmaceutically acceptable acid addition salt form. Such acid addition salt forms exhibit the same order of activity as the free base forms. The present invention also provides a pharmaceutical composition comprising a compound of the invention, in free base form or in pharmaceutically acceptable acid addition salt form, in association with a pharmaceutical carrier or diluent. Such compositions may be in the form of, for example, a solution or a tablet.

The neuroleptic activity is the preferred utility. The preferred compound is the Example 1 compound. This has been found active in the inhibition of spontaneous motor activity in mice of from 32 mg/kg p.o., in the sleep/wake cycle in rat at 10 mg/kg p.o. and in the inhibition of cortical noradrenaline uptake in vivo in rat at 40 to 150 mg/kg i.p.

In one group of compounds $R_1$ is hydrogen, halogen or $(C_{1-3})$-alkyl, $R_2$ is hydrogen, $(C_{1-4})$alkyl, $(C_{2-4})$hydroxyalkyl or alkanoyl$(C_{1-4})$oxyalkyl, $R_3$ is hydrogen, $(C_{1-4})$alkyl or benzyl and $R_4$ is hydrogen.

In a first group of compounds $R_1$ is hydrogen.
In a second group of compounds $R_1$ is halogen.
In a third group of compounds $R_1$ is alkyl.
In a fourth group of compounds $R_1$ is alkoxy.
In a fifth group of compounds $R_1$ is alkylthio.
In a sixth group of compounds $R_1$ is trifluoromethyl.
In a seventh group of compounds $R_4$ is hydrogen.
In an eighth group of compounds $R_4$ is halogen.
In a ninth group of compounds $R_4$ is alkyl.
In a tenth group of compounds $R_4$ is alkoxy.
In an eleventh group of compounds $R_4$ is alkylthio.
In a twelfth group of compounds $R_4$ is trifluoromethyl.
In a thirteenth group of compounds $R_2$ is hydrogen.
In a fourteenth group of compounds $R_2$ is alkyl.
In a fifteenth group of compounds $R_2$ is hydroxyalkyl.
In a sixteenth group of compounds $R_3$ is hydrogen.
In a seventeenth group of compounds $R_3$ is alkyl.
In an eighteenth group of compounds $R_3$ is benzyl.

What we claim is:

1. A compound of formula I,

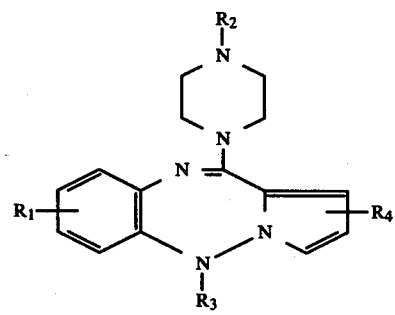

wherein
- $R_1$ and $R_4$ are each independently hydrogen, halogen, $(C_{1-4})$alkyl, $(C_{1-4})$alkoxy, $(C_{1-4})$alkylthio or trifluoromethyl,
- $R_2$ is hydrogen, $(C_{1-4})$alkyl, $(C_{2-4})$-hydroxyalkyl or alkanoyl $(C_{1-4})$-oxyalkyl, and
- $R_3$ is hydrogen, $(C_{1-4})$alkyl, $(C_{3-5})$alkenyl or benzyl, said compound being in free base or in pharmaceutically acceptable acid addition salt form.

2. A compound of claim 1 wherein $R_1$ is hydrogen, halogen or $(C_{1-3})$alkyl, $R_2$ is hydrogen, $(C_{1-4})$alkyl, $(C_{2-4})$hydroxyalkyl or alkanoyl$(C_{1-4})$oxyalkyl, $R_3$ is hydrogen, $(C_{1-4})$alkyl or benzyl and $R_4$ is hydrogen, said compound being in free base or in pharmaceutically acceptable acid addition salt form.

3. The compound of claim 1 which is 8-chloro-5-methyl-11-(4-methyl-1-piperazinyl)-5H-pyrrolo[1,2-b][1,2,5]benzotriazepine, said compound being in free base or in pharmaceutically acceptable acid addition salt form.

4. The compound of claim 1 which is 11-(4-methyl-1-piperazinyl)-5H-pyrrolo[1,2-b][1,2,5]benzotriazepine, said compound being in free base or in pharmaceutically acceptable acid addition salt form.

5. The compound of claim 1 which is 5-methyl-11-(4-methyl-1-piperazinyl)-5H-pyrrolo[1,2-b][1,2,5]benzotriazepine, said compound being in free base or in pharmaceutically acceptable acid addition salt form.

6. The compound of claim 1 which is 8-fluoro-5-methyl-11-(4-methyl-1-piperazinyl)-5H-pyrrolo[1,2-b][1,2,5]benzotriazepine, said compound being in free base or in pharmaceutically acceptable acid addition salt form.

7. The compound of claim 1 which is 5-methyl-11-(1-piperazinyl)-5H-pyrrolo[1,2-b][1,2,5]benzotriazepine, said compound being in free base or in pharmaceutically acceptable acid addition salt form.

8. The compound of claim 1 which is 8-chloro-3,5-dimethyl-11-(4-methyl-1-piperazinyl)-5H-pyrrolo[1,2-b][1,2,5]-benzotriazepine, said compound being in free base or in pharmaceutically acceptable acid addition salt form.

9. The compound of claim 1 which is 8-bromo-5-methyl-11-(4-methyl-1-piperazinyl)-5H-pyrrolo[1,2-b][1,2,5]benzotriazepine, said compound being in free base or in pharmaceutically acceptable acid addition salt form.

10. The compound of claim 1 which is 5-methyl-11-(4-methyl-1-piperazinyl)-8-trifluoromethyl-5H-pyrrolo[1,2-b][1,2,5]-benzotriazepine, said compound being in free base or in pharmaceutically acceptable acid addition salt form.

11. The compound of claim 1 which is 8-chloro-3-methyl-11-(4-methyl-1-piperazinyl)-5H-pyrrolo[1,2-b][1,2,5]benzotriazepine, said compound being in free base or in pharmaceutically acceptable acid addition salt form.

12. The compound of claim 1 which is 8-chloro-11-(4-methyl-1-piperazinyl)-5H-pyrrolo[1,2-b][1,2,5]benzotriazepine, said compound being in free base or in pharmaceutically acceptable acid addition salt form.

* * * * *